US010259398B2

(12) United States Patent
Naboulsi

(10) Patent No.: US 10,259,398 B2
(45) Date of Patent: Apr. 16, 2019

(54) SYSTEM FOR CONTROLLING TELEMATICS AND VEHICLES TO REDUCE DRIVER OVERLOAD AND DISTRACTION

(71) Applicant: Mouhamad A. Naboulsi, West Bloomfield, MI (US)

(72) Inventor: Mouhamad A. Naboulsi, West Bloomfield, MI (US)

(*) Notice: Subject to any disclaimer, the term of this patent is extended or adjusted under 35 U.S.C. 154(b) by 428 days.

(21) Appl. No.: 13/628,884

(22) Filed: Sep. 27, 2012

(65) Prior Publication Data

US 2013/0036841 A1 Feb. 14, 2013

Related U.S. Application Data

(63) Continuation of application No. 10/287,299, filed on Nov. 4, 2002, now Pat. No. 6,731,925, which is a continuation of application No. 10/279,447, filed on Oct. 24, 2002, now abandoned.

(60) Provisional application No. 60/390,877, filed on Jun. 21, 2002, provisional application No. 60/336,293, filed on Oct. 24, 2001.

(51) Int. Cl.
| | |
|---|---|
| *H04B 1/38* | (2015.01) |
| *B60R 11/02* | (2006.01) |
| *G08B 21/06* | (2006.01) |
| *A61B 5/18* | (2006.01) |
| *B60R 11/00* | (2006.01) |
| *H04M 1/60* | (2006.01) |

(52) U.S. Cl.
CPC ............. *B60R 11/02* (2013.01); *G08B 21/06* (2013.01); *A61B 5/18* (2013.01); *B60R 11/0264* (2013.01); *B60R 2011/001* (2013.01); *B60W 2520/10* (2013.01); *B60W 2540/12* (2013.01); *H04M 1/6041* (2013.01)

(58) Field of Classification Search
CPC .......... G08B 3/10; B60N 3/102; B60N 3/103; B60N 3/104; B60N 3/106; B60N 3/108; H05B 3/026; H05B 3/26; A47G 23/0225
USPC ......... 248/311.2, 346.11; 296/24.34; 446/81; 455/411, 414.2; 62/3.61, 3.64; 340/545.6; 219/438; 392/498
See application file for complete search history.

(56) References Cited

U.S. PATENT DOCUMENTS

| | | | | |
|---|---|---|---|---|
| 4,546,237 A | * | 10/1985 | Collins | 392/498 |
| 4,760,987 A | * | 8/1988 | Lan | 248/346.11 |
| 4,941,635 A | * | 7/1990 | Lan | 248/346.11 |

(Continued)

FOREIGN PATENT DOCUMENTS

| | | | |
|---|---|---|---|
| KR | 1998/060960 | * | 10/1998 |
| KR | 2001/0000992 | * | 1/2001 |

*Primary Examiner* — An T Nguyen

(57) ABSTRACT

In accordance with the present invention there is provided a comestible holder or retention device or retainer for sensing, controlling and monitoring driver access to food or drink while operating a vehicle. Preferably, the retainer comprises either a cup holder or a tray which retains comestible containers or the comestible, itself, in a reasonably stable position. The present invention further includes means for indicating the status of the comestible retainer as well as the comestible, itself, to the driver or other personnel and/or device to minimize preoccupation and distraction from driving while trying to determine the status of the foodstuff. Thus, the present device is utilized in conjunction with vehicular disposed telematics and is in communication therewith.

23 Claims, 5 Drawing Sheets

(56) References Cited

U.S. PATENT DOCUMENTS

| | | | |
|---|---|---|---|
| 5,601,269 A * | 2/1997 | Jankovic | 248/311.2 |
| 6,082,114 A * | 7/2000 | Leonoff | 62/3.64 |
| 6,450,587 B1 * | 9/2002 | MacGregor et al. | 303/89 |
| 6,719,343 B2 * | 4/2004 | Emerling et al. | 296/24.34 |
| 8,104,295 B2 * | 1/2012 | Lofy | 62/3.61 |
| 2002/0171018 A1 * | 11/2002 | Harada | 248/311.2 |
| 2002/0173889 A1 * | 11/2002 | Odinak et al. | 701/36 |
| 2003/0083079 A1 * | 5/2003 | Clark et al. | 455/466 |
| 2003/0096593 A1 * | 5/2003 | Naboulsi | B60R 11/02 455/411 |
| 2004/0209594 A1 * | 10/2004 | Naboulsi | B60R 11/0264 455/404.1 |
| 2005/0109767 A1 * | 5/2005 | Fennewald | B29C 45/2737 219/543 |
| 2005/0205739 A1 * | 9/2005 | DePue | B60N 3/106 248/311.2 |
| 2005/0257531 A1 * | 11/2005 | Kadle | B60H 1/00285 62/3.3 |
| 2006/0208881 A1 * | 9/2006 | Suzuki | A01N 1/02 340/539.27 |
| 2008/0033610 A1 * | 2/2008 | Engel | G06F 1/182 701/36 |
| 2008/0149300 A1 * | 6/2008 | Matsukawa | B60N 3/104 165/43 |
| 2009/0224564 A1 * | 9/2009 | O'Brien | B60N 2/4686 296/37.8 |
| 2009/0239440 A1 * | 9/2009 | Kang | 446/81 |
| 2009/0288800 A1 * | 11/2009 | Kang | B60N 2/4686 165/42 |
| 2012/0103562 A1 * | 5/2012 | Alexander | A47J 36/2466 165/64 |
| 2012/0217772 A1 * | 8/2012 | Tang | B60N 3/104 297/188.01 |
| 2012/0282906 A1 * | 11/2012 | Frye | H04W 4/04 455/414.2 |
| 2013/0036841 A1 * | 2/2013 | Naboulsi | B60R 11/02 73/865.8 |
| 2013/0098893 A1 * | 4/2013 | Soule | A47J 36/2461 219/441 |
| 2013/0175250 A1 * | 7/2013 | Saatkamp | A47J 36/2483 219/387 |
| 2015/0165953 A1 * | 6/2015 | Oh | B60N 3/104 62/3.3 |
| 2015/0165954 A1 * | 6/2015 | Oh | B60N 3/104 62/3.3 |
| 2016/0023585 A1 * | 1/2016 | Salter | B60N 3/104 165/202 |
| 2016/0339822 A1 * | 11/2016 | Park | B60N 3/104 |
| 2017/0144577 A1 * | 5/2017 | Oh | B60N 3/104 |

\* cited by examiner

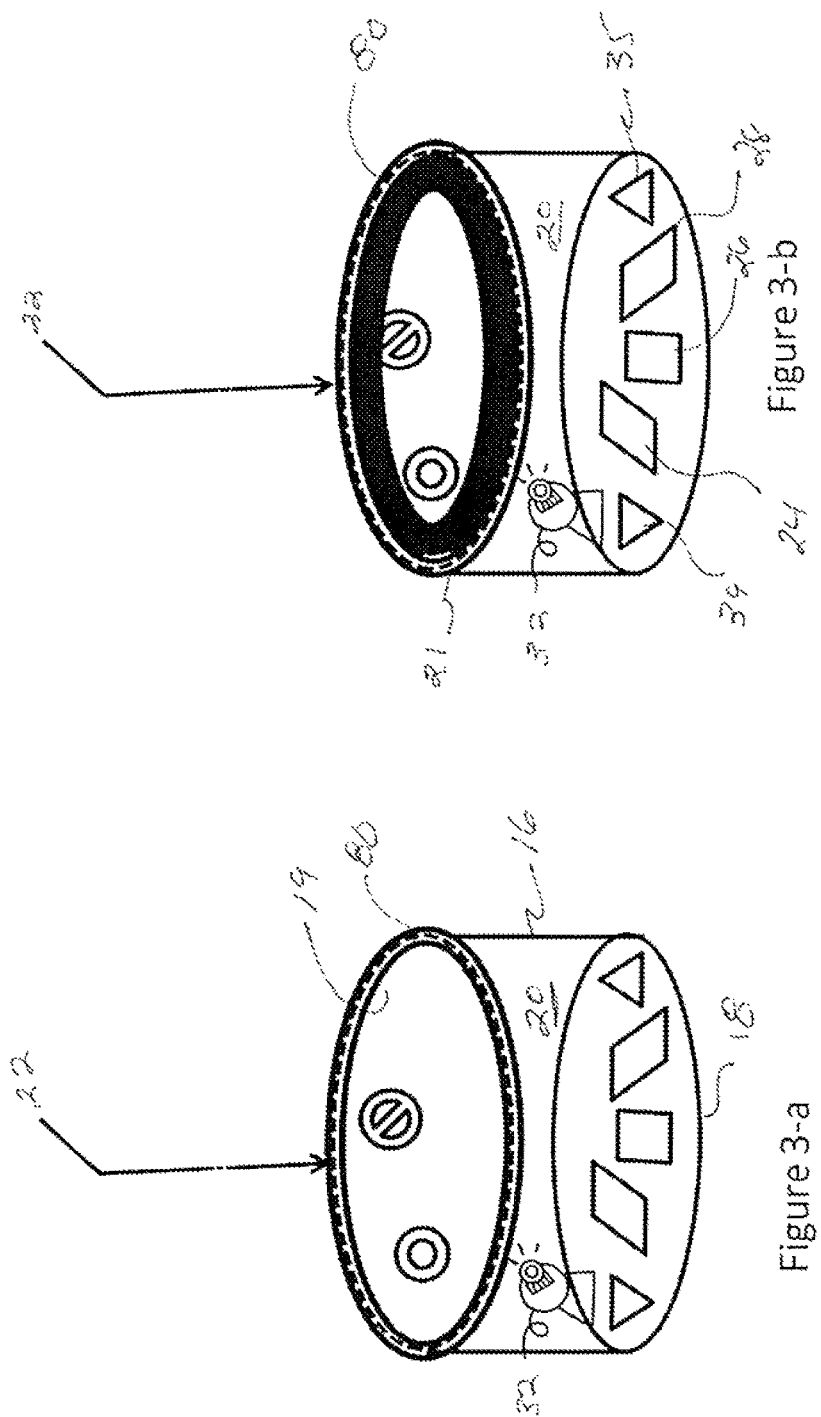

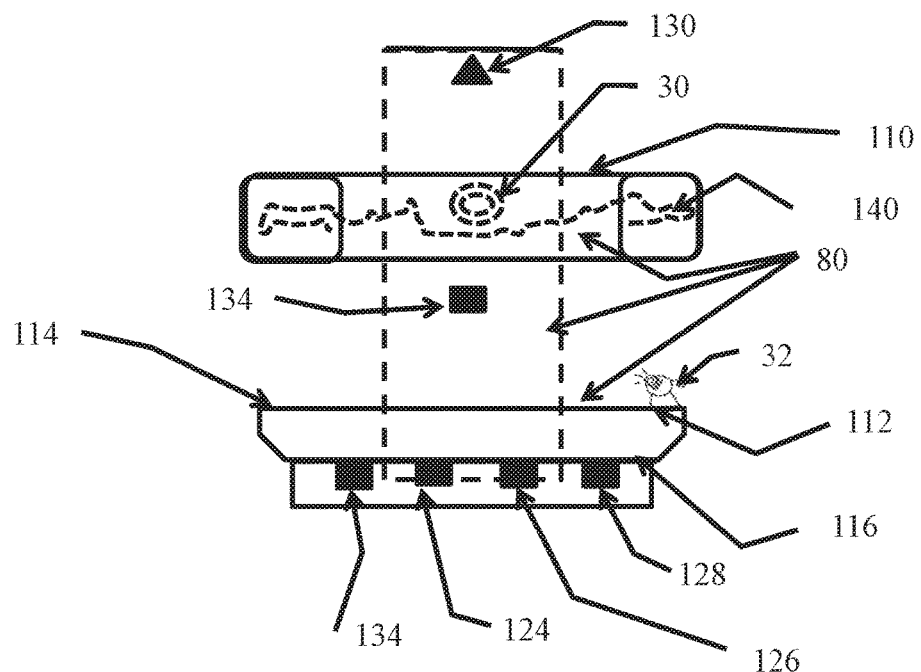
Figure 4A
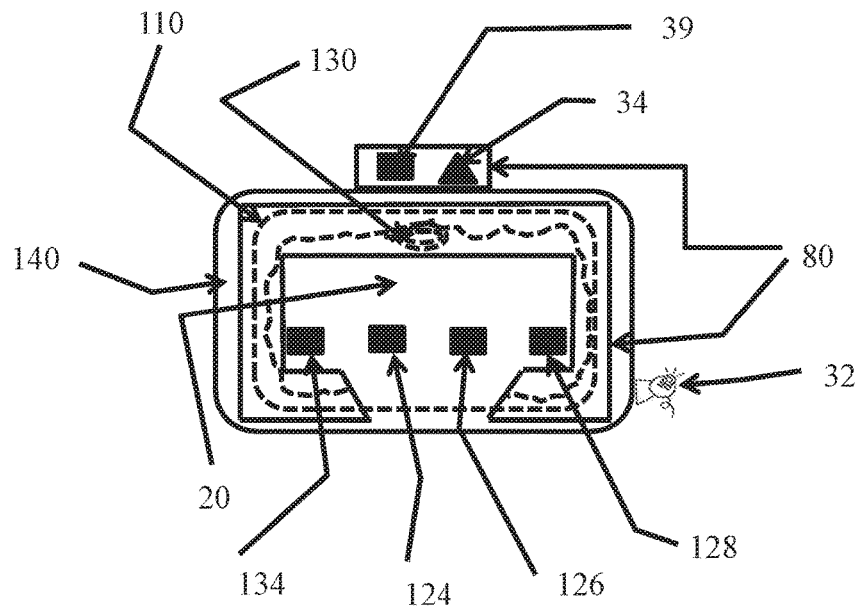
Figure 4B
Figure 4

SYSTEM FOR CONTROLLING TELEMATICS AND VEHICLES TO REDUCE DRIVER OVERLOAD AND DISTRACTION

CROSS REFERENCE TO RELATED APPLICATIONS

This application is a continuation-in-part application of co-pending U.S. patent application Ser. No. 10/838,708, filed May 4, 2004 which is a continuation of Ser. No. 10/287,299, filed Nov. 4, 2002, which claims the benefit of and priority from U.S. patent application Ser. No. 10/279,447, filed Oct. 24, 2002, Provisional Application No. 60/336,293, filed Oct. 24, 2001, and Provisional Application No. 60/390,877, filed Jun. 21, 2002, the entire contents each of which are incorporated herein by reference.

BACKGROUND OF THE INVENTION

1. Field of the Invention

The present application pertains to the utilization of vehicular food retention devices coupled to telematics in vehicles. More particularly, the present invention pertains to the use of such devices to control the consumption as well as stabilize the retention thereof in the device as well as to sense other properties associated with vehicle dynamics and dangerous conditions. Even more particularly, the present invention pertains to the utilization of such retention devices in a system, including, remote devices, where such devices are coupled to telematics disposed within a vehicle.

2. Description of the Prior Art

In the above-identified co-pending application there is disclosed the utilization of telematics to minimize driver distraction while operating a vehicle. The telematics devices include vehicle sensors, per se, incorporated into the steering wheel of the vehicle and to other vehicle controls such as the brakes, accessories, powertrain and which may be coupled to portable devices such as cell phones, PDAs etc.

One of the contemplated features disclosed therein is the provision for sensing, controlling and monitoring a driver's access to comestible items which include at least food or beverage and the like while operating the vehicle. The present invention further details improvements therein.

SUMMARY OF THE INVENTION

In accordance with the present invention there is provided a comestible holder or retention device or retainer for sensing and thereby controlling and monitoring driver access to food or drink while operating a vehicle. Preferably, the retainer comprises either a cup holder or a tray which retains comestible containers or the comestible, itself, in a reasonably stable position.

The present invention further includes means for indicating the status of the comestible retainer as well as the comestible, itself, to the driver or other personnel and/or device to minimize preoccupation and distraction from driving while trying to determine the status of the foodstuff. Thus, the present device is utilized in conjunction with vehicular disposed telematics and is in communication therewith.

The retention device generally comprises:
(a) a housing for removably emplacing a food comestible container therewithin or therein;
(b) means for sensing the presence of a comestible item or its container on or in the device;
(c) means for retaining the comestible item or its container on or in the device;
(d) means for signaling to a controller at least one of:
  (i) the presence of a comestible item or its container to a controller;
  (ii) the condition of the comestible item or its container that includes at least the temperature, the weight, and the; and
  (iii) the type of comestible item.

Preferably, the means for signaling comprises a plurality of sensors for each of the signaled conditions.

Additional sensors which may be incorporated into the device include an optical sensor for reading a barcode or the like on the container as well as a gas emission sensor, an RFID sensor probing signal to detect an RFID sensor and receives such signals back from the sensor on the comestible, item or its container and sends to the controller.

The retention device is formed from any suitable polymeric material to enable it to be changed or shaped to engage a container or a comestible item, itself, to stabilize it within or on the device. Suitable materials of construction include polymeric, shape changing bimetals or inflatable materials.

In another aspect hereof, there is provided a system utilizing the present retention device according hereto, the device being displayed in conjunction with a controller. The controller is in communication with the device and senses, stores and intercepts data received from the sensors. The controller is responsive to the signals generated by the sensor and, therefrom, directs and/or controls any necessary active action or consequence thereof.

Other features and advantages of the present invention will become apparent from the following detailed description and accompanying drawings. In the drawing like reference characters refer to like parts throughout the several means in which:

BRIEF DESCRIPTION OF THE DRAWINGS

FIG. 3a is a perspective view of a cup holder in accordance with the present invention;

FIG. 3b is a perspective view of a same embodiment of the cup holder of the present invention showing an actuated retention mechanism;

FIG. 4a is a side view of a second embodiment hereof;

FIG. 4b is a top view of the embodiment of FIG. 4a;

DETAILED DESCRIPTION OF THE PREFERRED EMBODIMENT

Figure 1:
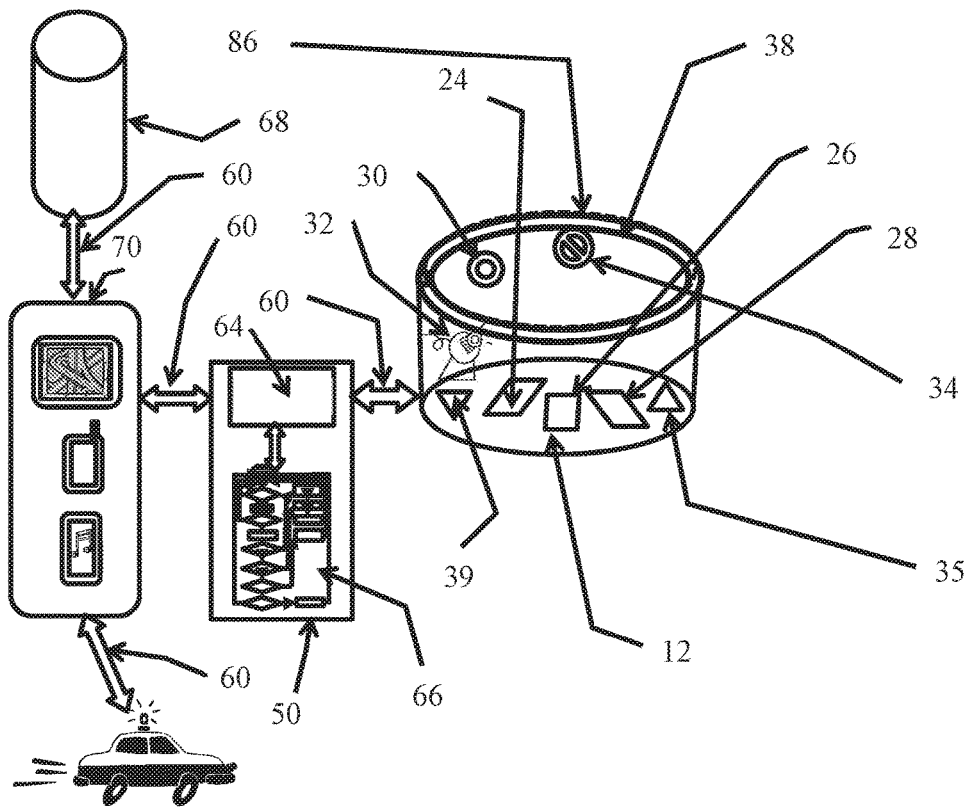
FIG. 1 is a flow chart showing one embodiment as a cup holder in accordance with the present invention.

Now, and according to the present invention and with reference to the drawing, and in particular FIGS. 1-3b there is depicted a system, generally, denoted at 10 for sensing, monitoring and controlling the consumption of food, whether solid or liquid, by a vehicle driver.

More specifically, there is provided a retention holder or device 12 such as a cup or a cup holder 14. The cup holder 14 has a cylindrical sidewall 16, a bottom wall 18 and an open top 19. The sidewall 16 and the bottom wall 18 cooperate to provide an open interior 20 in which is removably disposed either a comestible item or foodstuff, itself, (not shown) or a container (not shown) therefor. For purposes of understanding the present invention, the ensuing description will be made in connection with a foodstuff container.

As shown, the holder 14 includes an upper peripheral lip 22 proximate a free end 21 of the sidewall 16, which, as described subsequently plays an integral part of the invention.

A series of sensors 24, 26, 28 and 30 are disposed on the bottom wall 18 or embedded therewith. Typically, such sensors will comprise a sensor 26 for detecting the presence of a container. A temperature sensor 28 senses the temperature of the container. A weight sensor 24 measures the weight of the container.

Additionally, sensors 30, 32 and 34 are disposed on the interior of the wall 18. Optimally, the sensor 30 is an RFID scanner that sends scanning signals for an RFID sensor which receives such signals back from a sensor on the comestible container and sends the signal to a controller 50 in a manner disclosed hereinafter.

The optical sensor 32 reads barcodes or the like and is able to transmit the information including the barcode to a controller 50.

Also, the optical sensor can work with at least another optical device to get multiple profile images to process. The optical sensor 32 can also serve to detect the presence of an item in the retention device using the same image processing capabilities by comparing the profile of the retention device to a stored base image of the device when it is empty.

Similarly, the temperature sensor can be an infrared sensor positioned above the device to remotely sense the temperature. The gas sensor 34 detects the presence of steam, noxious fumes, alcohol fumes or the like and similarly transmits signals to the controller 50. The gas sensor also can be placed above or near the retention device.

The RFID scanner 30 can be placed anywhere in the vehicle and its detection can be used with other accessories to it is universally used in the vehicle and need not be dedicated for just the comestible item retention device.

The bottom wall or base 18 of the holder 12 is further equipped with means for facilitating the retention of a container therewithin. A vacuum retention member 35 disposed on the wall 18 is used to create a negative pressure via a source V to facilitate the retention of a container within the interior 20 of the holder 12. The vacuum is applied by any suitable means such as an exhaust pump, or the like (not shown) which may be powered from a vehicular battery or have an independent power source. Alternately, the vacuum source can be supplied from the engine through a suitable vacuum hose or pipe with a solenoid valve, electrically connected to the controller to trigger a valve open condition when a container presence is detected.

Additionally, depending on the nature of the material of construction of the container, the retention and maintaining of the container within the interior of the holder may be facilitated through the use of an electromagnetic retention device 39. The electromagnetic retention device 39 generally, comprises a magnet coil of insulated electrical conductors which generates a magnetic field when an electrical current is applied to it, which attracts and holds the container within the interior of the holder. Such a coil may be powered through the vehicle battery or an independent power source.

It is further contemplated that the interior of the retention device may be heated to keep the interior 20 warm, for example, via a heating element 38, which is disposed, preferably, at the upper lip of the cylindrical wall 16. Optionally, a thermoelectric effect heating and cooling module may be embedded into the holder so the contents can be heated and/or cooled.

As noted hereinabove it is desirable for the opening into the interior of the holder be altered, i.e., narrowed. Thus, an expansible body 80 is disposed proximate the upper end or free end of the wall 16 and the opening into the interior 20 of the device 12. The body 80 may be heat, vacuum, pressure or electrically actuated to cause an expansion thereof and, thereby, constrict the entry into the interior opening. The body is expansible to enable gripping of the container disposed within the holder. Representative materials for the body which enable this expansion include, for example, shape memory polymer, shape memory alloys, inflatable materials and the like.

A suitable memory polymer can be shaped to grasp and collapsed to conform to the shape of the container removably stowed therewithin.

In operation the sensors as well as the retention mechanisms are powered through an electrical input in the well known manner.

Figure 2:
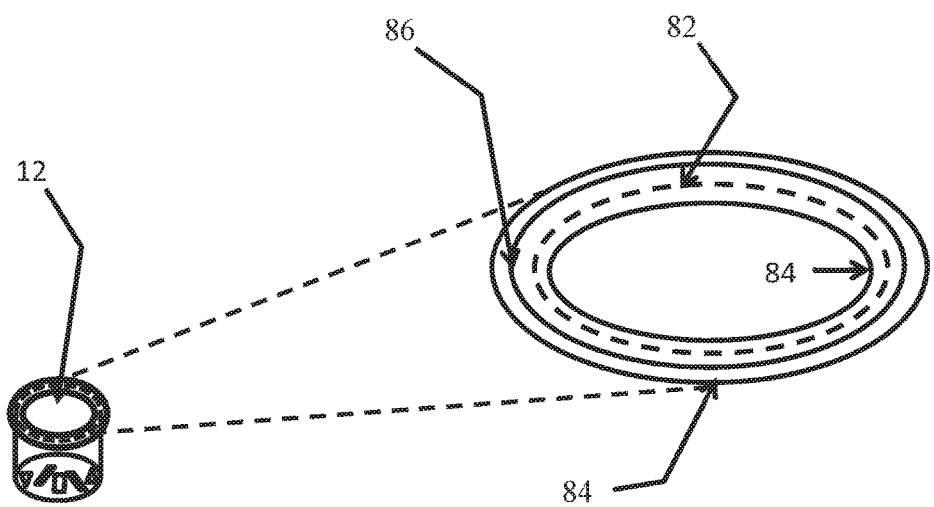
FIG. 2 is a schematic of the heating element used in accordance herewith.

In FIG. 2 the detail of the body 80 is shown therein. As shown the body 80 is essentially a toroidal member, and comprises an expansion member 82. An insulation or insulating member surrounds the member 82 and prevents heat from escaping outside the device 12. The insulating member 84 can be formed from any suitable material such as a dielectric, rubber, synthetic polymer or the like. An actuating element 86 is used to expand the member 39 into the opening into interior of the holder. The element 86 may be actuated by any suitable energy source such as heat, electricity, vacuum or pressure.

As noted hereinabove, a source of energy, such as electricity or the like, (not shown), is used to power the body 80.

Alternatively, the body 80 may be initially under vacuum and when the vacuum is released, the material returns to its original shape and expands into the interior. A pressure relief valve (not shown) of the type well known to the skilled artisan can then be associated therewith to retract or release the body 80. Suitable polymers for the body 80 include shape memory polymers as well as shape memory alloy that can be actuated by temperature or electrical current, and other materials suitable for holding fluids, including gasses.

Referring again to FIG. 1 the device or holder 12 is in electrical communication with the controller 50. The holder 12 and the controller 50 cooperate to define a system for sensing, controlling and monitoring the contents within the holder 12. Communication therebetween can be established through many suitable means, such as, for example, an electrical bus 60 or wireless communication that enables transmission of data via signals through the RFID sensor or the like. The electrical wires can be sourced from a battery, or from a self-contained battery pack or the like.

The controller comprises a housing 63 having a pc board 64 comprising a logic program stored therewithin. The controller 50 further comprises a microchip having program logic and which is connected to a CPU or other memory storage device 66 which is internally stored within the controller housing.

The controller 50 is, preferably, operatively connected to data storage device 68 disposed in the vehicle, but may be remote from the vehicle. The storage device 68 is, in and of itself, preferably, connected to a telematics console or device 70, such as disclosed in the above-identified co-pending application.

The communication link between the controller 50 and the storage device 68 and the telematics device 70 can be achieved through any suitable means in the same manner as described hereinabove.

In use, the controller receives the driver preferences from a memory medium by downloaded messages or by accessing a database in the vehicle or from a remote location. The preferences concern the food and beverage types preferred by the driver and the preferred temperatures of the comestible. Advantageously, the controller will monitor the driver usage for each type of item contained within the holder to pattern methods of retrieving from and or returning an item to the holder. The preferences will be for types of items and their physical status, thereby minimizing driver distraction.

The controller further includes means to accept policies that can be customized by parents, insurance companies other authorities. The controller will also enables precluding or delaying phone calls and other low priority notifications each time a driver removes an item from the holder. However, the controller will release calls to the driver when the driver puts an item back in the holder. Further, the controller can be programmed for incoming announcements and ongoing conversation while it will not disconnect an ongoing telematics voice/data communication but will place a hold on a temporal, geographical, heading, bearing, traffic or weather factor where a food or beverage is known and/or likely to lead to an accident.

Referring now to FIG. 4 there is depicted therein an alternate embodiment of the retention device hereof and which is generally denoted at 110. Here, the device 110 comprises a tray 112 upon which is seated a comestible item(s) (not shown) or a container for a food stuff.

The tray, generally, comprises an upper surface 114 and a bottom surface 116.

Sensors 124, 126 and 128 correspond to the sensors 24, 26, 28 associated with the first embodiment hereof and are used in a similar manner as that described hereinabove. The sensors may be embedded directly into the bottom wall 116 or may be disposed within a suitable housing 130, as shown, and which are in contact with the container or the foodstuff itself.

Similarly, elements 132 and 134 operate in the same manner as described with respect of elements 32 and 34 of the first embodiment.

Here, however, a tower 137 has the sensor 134 disposed proximate the top thereof for detecting gasses and an RFID sensor 130 for receiving and transmitting signals.

A wall 140 is used to envelope a container for a comestible item(s) itself. The wall is similarly constructed material-wise as that hereinabove described. The wall 140 may be collapsible to envelope and encircle a container.

A heating element (not shown) may be hardwired into the arm to keep food stuffs warm.

In all other respects the holder hereof operates the same as with respect to the first embodiment and, similarly, is controlled by a suitable controller (not shown).

Figure 5:
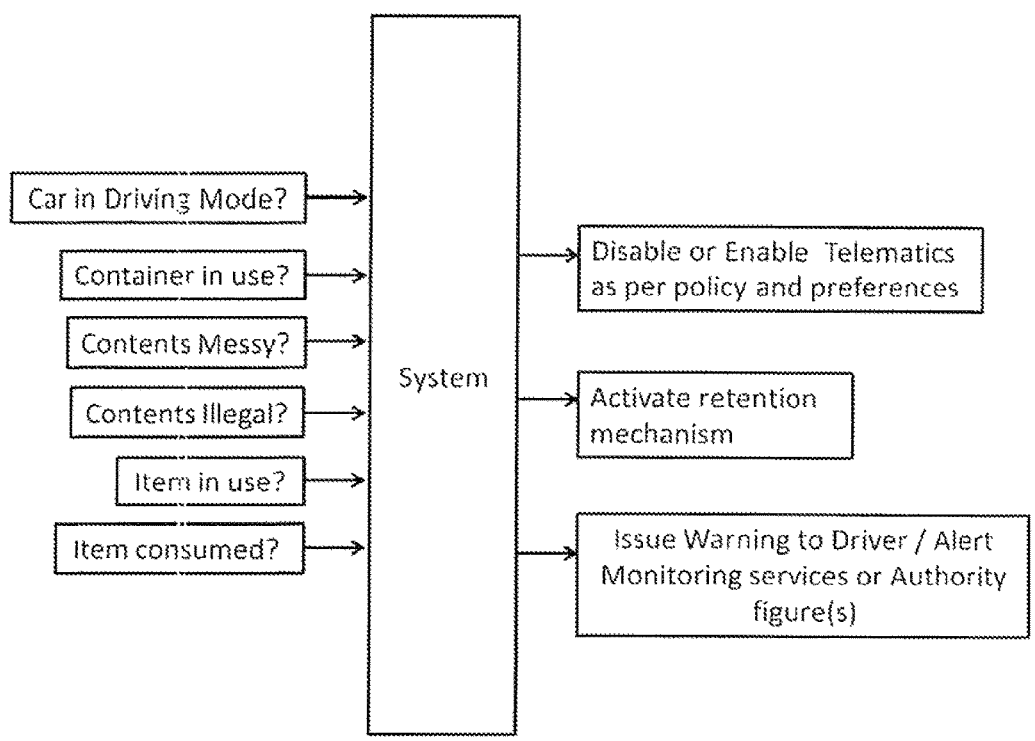
FIG. 5 is a system block diagram.

Referring now to FIG. 5 there is shown therein a schematic showing a block diagram of the manner by which the various sensors relay information to the controller which, in turn, sends out the appropriate signals for appropriate operation.

Figure 6:
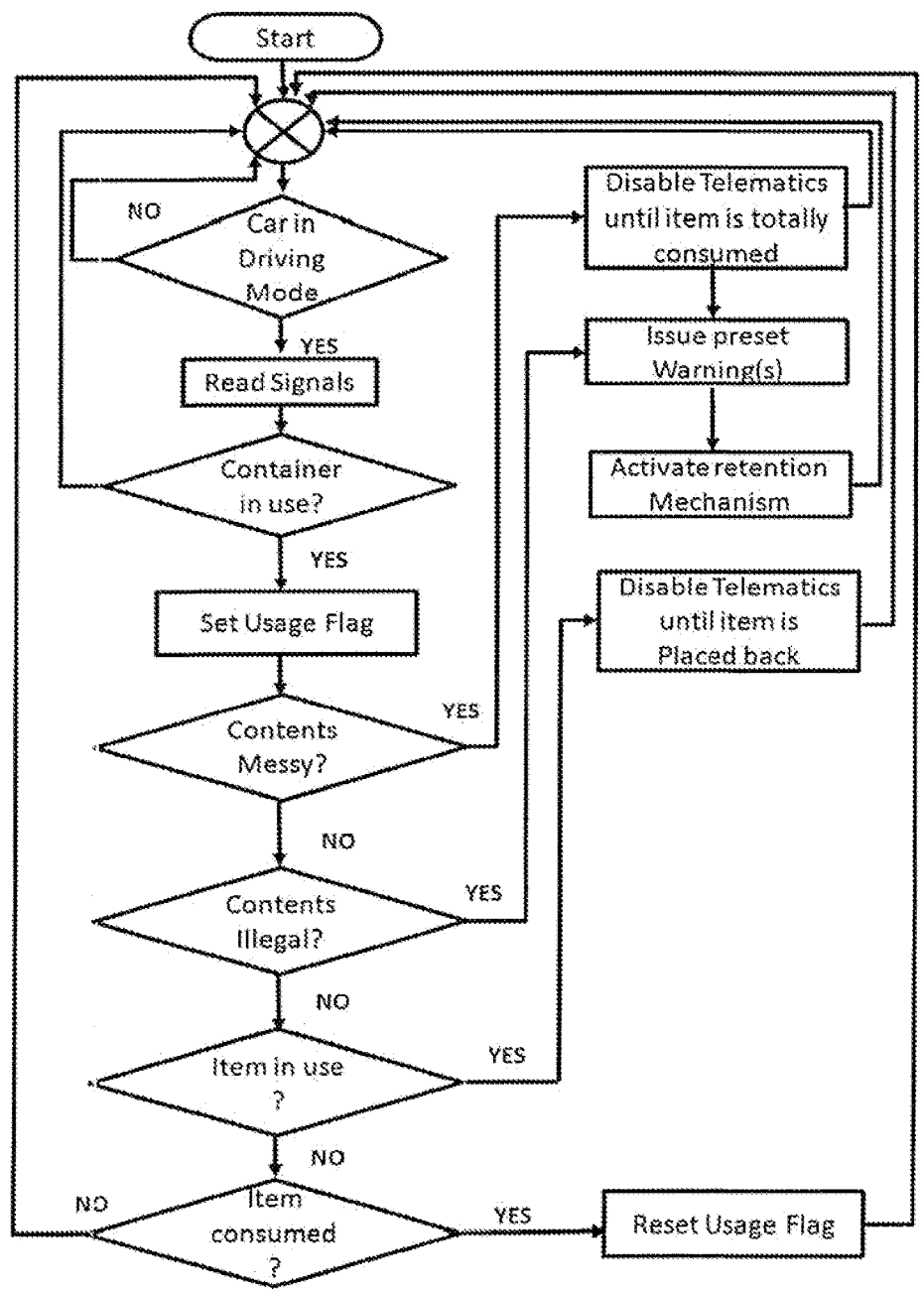
FIG. 6 is a flowchart showing the operation of the retainer in accordance with the present invention.

FIG. 6 illustrates the logic circuit maintained within the controller and the appropriate responses which are transmitted or not transmitted back to the device 12 or 110.

The controller in addition to sensing the conditions within the device, itself, can be connected through a telematics unit as noted hereinabove. In addition the controller can be remotely operated by a LAN, WAN, an Internet processing center or server(s) communicating with the controller via radio transmission a V2V or V2I network. Once the controller has "learned" the preferences of the driver, they can be stored within the memory or can be downloaded from a database contained within the controller or wirelessly from a remote location wirelessly. These preferences can be tagged in any suitable manner, such as environmental, medical factors, for hydration purposes. The controller may be voice-equipped to give the driver a verbal reminder in a manner well known to the skilled artisan.

Thus, the present invention provides an intelligent food and beverage retention device that is responsive to the driver; manages food or beverage items placed in the holder in consideration to the driver preferences the driver preferred disposition communicates with telematics devices. In conjunction with the telematics devices, it can be determined when the driver can answer a call or while he is drinking or eating.

The controller can act upon such recognition(s) by decreasing unnecessary distractions from announcements and Telematics, giving the driver more time to respond to a non-driving critical request for action, e.g., answering a phone while placing an item back in the retention device. Additionally, the controller can disable a car from moving or can notify authorities, if the item being detected is illegal. It should be noted that while the holder or retention device hereof has been described with respect to their respective sensors being directly mounted to or embedded therewithin, it is possible to place the sensors in proximity to the holder in a manner such that they can still sense their respective functions.

Hence, the optical sensor, the temperature sensor, the RFID scanner and the gas sensor can be placed outside the retention device but positioned in a manner that can still detect the device characteristics. For example, the optical sensor may have image recognition processing capability and when positioned above the retention device in an manner that enables it to see at least one profile of the item within the device, it can capture the image and process it in the controller using or on a remote controller, to determine its brand, its physical qualities, e.g. mushy, solid, etc.

It is further contemplated that the interior of the retention device may be heated to keep a disposed item warm, for example, via a heating element 76, which is disposed, preferably, at the upper lip of the cylindrical wall 16. Optionally, the retention holder may accommodate or embed a thermoelectric effect heating. The thermoelectric effect is a direct conversion of temperature differences to electric voltage and vice-versa. A thermoelectric device creates a voltage when there is a different temperature on each side. Conversely, when a voltage is applied to it, it creates a temperature difference. At the atomic scale, an applied temperature gradient causes charge carriers in the material to diffuse from the hot side to the cold side.

Further, with respect to the cup holder it can be placed in an existing vehicle cup well whereas the tray may be placed on a console of the type disposed between the seats. Similarly, the cup holder may have any geometric shape, as described.

The controller monitoring is adaptive to driver comestible item consumption habits, i.e., drive preferences and can correlate such consumption to time of day, time of year and location as well as driving habits and weather conditions. In response to input, the controller can automatically activate a heating or cooling function based on previous driver actuation of such capabilities. For example, in the winter, the driver may place a room temperature drink container and actuate a heating switch but in the summer, the driver can actuate a cooling switch. The controller stores such activity and will actuate the proper function regardless of the temperature of the container. Similarly, the controller can actuate the heating or cooling element depending on a geographic location and time of day or year as a trigger. The controller may also use the location association and the time of day or year association to actuate the heating or the cooling function automatically. The benefit is that the driver will not have to participate in manual visual task which is likely to be done while driving so such feature will reduce distraction.

From the preceding it is apparent there has been described herein a "intelligent" retention device for retaining food stuff directly or within suitable containers therefore and which when operatively connected to telematics can control the drinking as well as the eating habits of the driver.

A monitoring service or suitable authority may be linked to the telematics console (not shown), if desired, through a wireless communication link in a manner well known to the skilled artisan, e.g. cellular device, LAN, WAN or Internet.

Having, thus, described the invention what is claimed is:

1. A device for monitoring the ingestion of a comestible in a vehicle and controlling a communication device, the device comprising:
   (a) a retention member for removably retaining a comestible container for holding a comestible therein or thereon;
   (b) a sensor associated with the retention member, the sensor signaling a property of the comestible in or on the comestible container, wherein the property is selected from at least one of a temperature of the comestible container, a presence of the comestible container within the retention member, a weight of the comestible container, and a type of the comestible within the comestible container; and
   c) a controller in communication with the sensor to receive a signal from the sensor about a property of the comestible in or on the comestible container wherein the controller controls the communication device by delaying phone calls and/or notifications from the communication device based on information received from the sensor.

2. The device of claim 1, wherein the retention member is a cup holder which removably receives a comestible with or without container.

3. The device of claim 2, wherein the cup holder has a side wall, a bottom wall and an open top, the sensor being disposed on the cup holder.

4. The device of claim 2, wherein the sensor is embedded in the cup holder.

5. The device of claim 2 which further comprises:
   means for expanding and narrowing the cup holder.

6. The device of claim 2 which comprises:
   a shapeable material, the material being conformable to the shape of the comestible container.

7. The device of claim 1, wherein the sensor is a sensor for measuring the temperature of the comestible container, an optical sensor for reading indicia on the comestible container, or a sensor for measuring the weight of the comestible container and the comestible.

8. The device of claim 1 which further comprises means for stabilizing the comestible container while being retained by the retention member.

9. The device of claim 1 further including means for stabilizing the comestible in the retention member during vehicle dangerous conditions.

10. The device of claim 1, which further comprises a thermoelectric effect sensor for heating or cooling the comestible.

11. The device of claim 1, wherein the retention member is a tray.

12. The device of claim 11, wherein at least one sensor is embedded in the tray.

13. The device of claim 11, wherein the sensor is a sensor for measuring the temperature of the comestible, an optical sensor for reading indicia for the comestible container, a sensor for measuring the weight of the comestible.

14. The device of claim 11 which further comprises means for stabilizing the comestible container while being retained by the retention member based on a sensed vehicle dynamics.

15. The device of claim 13, further including means for stabilizing the comestible container in the retention member during vehicle dangerous conditions.

16. The device of claim 11, which further comprises a thermoelectric effect sensor for heating or cooling the comestible.

17. A system for sensing, monitoring and controlling a communication device based on driver ingestion of a comestible in a vehicle comprising:
   (a) a retention member for removably retaining a comestible container having a comestible therein or thereon;
   (b) a controller, the controller receiving signals from at least one sensor to monitor sensed conditions of the comestible in the comestible container in the retention member, wherein the sensed conditions are a temperature of the comestible container, a presence of the comestible container within the retention member, a weight of the comestible container, and/or a type of the comestible within the comestible container, the gaseous property of the comestibles in or near the retention member, and wherein the controller is designed and configured to control the communication device by delaying phone calls and/or notifications from the communication device based on the driver interaction with the comestible.

18. A method for sensing a comestible in a vehicle to control a communications device, the method comprising:
   (a) removably retaining a comestible;
   (b) sensing conditions of the comestible, wherein the sensed conditions are a temperature of the comestible, a presence of the comestible within the retention member, a weight of the comestible, and/or a type of the comestible within the comestible container;
   (c) monitoring the driver interaction with the comestible; and
   (d) controlling the communication device by delaying phone calls and/or notifications from the communication device based on the sensed conditions of the comestible.

19. The method of claim 18 further comprising sending information about the sensed conditions of the comestible to a service or authority.

20. The device of claim 1 wherein the sensors are located inside a vehicle and send a signal detectable inside or outside the vehicle.

21. The device of claim 1 wherein the signal is about the disposition of the comestible.

22. The device of claim 1 wherein the signal is about elapsed time between removal and retention of comestible.

23. The device of claim 1 wherein the signal is about elapsed time between changes in the property of comestible.

\* \* \* \* \*